(12) United States Patent
Kawabata et al.

(10) Patent No.: US 10,688,485 B2
(45) Date of Patent: Jun. 23, 2020

(54) SUBSTRATE ANALYSIS NOZZLE AND METHOD FOR ANALYZING SUBSTRATE

(71) Applicant: IAS Inc., Tokyo (JP)

(72) Inventors: Katsuhiko Kawabata, Tokyo (JP); Sungjae Lee, Tokyo (JP)

(73) Assignee: IAS, INC, Tokyo (JP)

( * ) Notice: Subject to any disclaimer, the term of this patent is extended or adjusted under 35 U.S.C. 154(b) by 207 days.

(21) Appl. No.: 15/780,925

(22) PCT Filed: Jul. 18, 2017

(86) PCT No.: PCT/JP2017/025852
§ 371 (c)(1),
(2) Date: Jun. 1, 2018

(87) PCT Pub. No.: WO2019/016847
PCT Pub. Date: Jan. 24, 2018

(65) Prior Publication Data
US 2019/0358622 A1   Nov. 28, 2019

(51) Int. Cl.
*B01L 3/02* (2006.01)
*G01N 1/02* (2006.01)
(Continued)

(52) U.S. Cl.
CPC .................. *B01L 3/02* (2013.01); *G01N 1/02* (2013.01); *G01N 1/28* (2013.01); *G01N 33/00* (2013.01);
(Continued)

(58) Field of Classification Search
CPC ..... B01L 2300/0832; B01L 3/02; G01N 1/02; G01N 1/28; G01N 2001/028; G01N 2033/0095; G01N 33/00
See application file for complete search history.

(56) References Cited

U.S. PATENT DOCUMENTS

| 5,884,846 A | * | 3/1999 | Tan | ........................ | B05B 7/0475 128/200.21 |
| 8,398,746 B2 | * | 3/2013 | Black | ................... | G01N 1/2202 95/78 |

(Continued)

FOREIGN PATENT DOCUMENTS

| JP | 05-256749 A | 10/1993 |
| JP | 10-092784 A | 4/1998 |

(Continued)

OTHER PUBLICATIONS

Extended European Search Report, EP 17882257.3 = PCT/JP2017/025852, dated Jan. 31, 2019.

*Primary Examiner* — Francis C Gray
(74) *Attorney, Agent, or Firm* — Roberts & Roberts, LLP

(57) ABSTRACT

The present invention provides a substrate analysis nozzle that reliably prevents a leakage (release) of analysis solution from the nozzle even in the case of a highly hydrophilic substrate and that collects the analysis solution with a high collection ratio after scanning. The present invention is directed to a substrate analysis nozzle configured to discharge an analysis solution from a tip of the substrate analysis nozzle onto a substrate, configured to scan a surface of the substrate using the discharged analysis solution, and configured to suck the analysis solution. The substrate analysis nozzle has a triple-tube structure made up of: a pipe through which the analysis solution is discharged and sucked; a first outer tube surrounding the pipe and surrounding the analysis solution used for scanning; and a second outer tube surrounding the first outer tube. The substrate analysis nozzle includes: first exhausting means including an exhaust path defined between the pipe and the first outer (Continued)

tube; and second exhausting means including an exhaust path defined between the first outer tube and the second outer tube.

2 Claims, 2 Drawing Sheets

(51) Int. Cl.
    *G01N 1/28*       (2006.01)
    *G01N 33/00*     (2006.01)

(52) U.S. Cl.
    CPC ........... *B01L 2200/0615* (2013.01); *B01L 2200/0684* (2013.01); *B01L 2300/0832* (2013.01); *G01N 2001/028* (2013.01); *G01N 2033/0095* (2013.01)

(56) References Cited

U.S. PATENT DOCUMENTS

| | | | | |
|---|---|---|---|---|
| 8,795,779 | B2* | 8/2014 | Brown | B05B 13/0207 |
| | | | | 427/345 |
| 2004/0261817 | A1* | 12/2004 | Araki | H01L 21/67051 |
| | | | | 134/2 |
| 2015/0357249 | A1* | 12/2015 | Kawabata | H01J 37/32449 |
| | | | | 438/14 |
| 2017/0160233 | A1* | 6/2017 | Kawabata | G01N 1/28 |
| 2019/0013248 | A1* | 1/2019 | Kawabata | G01N 1/14 |

FOREIGN PATENT DOCUMENTS

| | | |
|---|---|---|
| JP | 2000-088717 A | 3/2000 |
| JP | 2011-128033 A | 6/2011 |
| JP | 2012-222254 A | 11/2012 |
| JP | 6156893 B | 5/2017 |

\* cited by examiner

SUBSTRATE ANALYSIS NOZZLE AND METHOD FOR ANALYZING SUBSTRATE

TECHNICAL FIELD

The present invention relates to a nozzle for analyzing an analysis subject such as a small amount of metal contained in a substrate. The present invention also relates to a method for analyzing a substrate using the nozzle.

RELATED ART

Nozzles for analyzing substrates such as semiconductor wafers are used to analyze a small amount of analysis solution to detect contaminants, such as metals and organic substances, that may have been contained in substrates through production processes. Specifically, a substrate analysis nozzle is used to analyze a substrate that is made up of: a base material such as a silicon wafer; and a film, such as a silicone oxide film and a nitride film, formed on the base material. After the formed film has been subjected to pre-treatment of vapor-phase decomposition or another method of etching, a small amount of analysis solution is discharged over the substrate, and the substrate surface with the discharged analysis solution is scanned using the substrate analysis nozzle. In the case of a hydrophobic substrate, because of surface tension, analysis solution more easily maintains a state of droplets on the surface of the hydrophobic substrate. This makes the above scanning of the substrate surface possible. By the scanning using the nozzle, metal and/or other substances on the substrate are caused to move into the analysis solution, and the analysis solution is collected using the nozzle and subjected to analysis.

A capability required of such substrate analysis nozzles is to efficiently analyze substrates in a short period of time even if the substrates are large in size. In an attempt to shorten the time necessary to scan the substrate surface, a known method is to increase the diameter of the nozzle orifice, thereby increasing the area of contact between the analysis solution and the substrate surface. Increasing the diameter of the nozzle orifice, however, makes the nozzle prone to release the analysis solution (the analysis solution is prone to leak through the tip of the nozzle) at the time of scanning. This may cause such another problem likely to occur that the analysis solution remains on the substrate after the scanning. In light of the circumstances, there is a need for a substrate analysis nozzle that has both of the two capabilities: to scan in a short period of time; and to make analysis solution difficult to release during scanning.

In Patent Document 1, the inventors propose a substrate analysis nozzle that has the above-described capabilities. The substrate analysis nozzle has a double-tube structure made up of: a nozzle body configured to discharge and suck analysis solution; and an outer tube disposed on the outer circumference of the nozzle body and surrounding the analysis solution used for scanning. In Patent Document 2, the inventors also propose a substrate analysis nozzle equivalent to the above substrate analysis nozzle of double-tube structure provided with a gas spraying tube. The gas spraying tube is configured to spray inactive gas toward the tip of the nozzle body in a direction approximately parallel to the substrate surface, and is disposed outside the outer tube, beside the tip of the outer tube, and at the side of the outer tube opposite to nozzle scanning direction.

RELATED ART DOCUMENTS

Patent Documents

[Patent Document 1]Japanese Unexamined Patent Application Publication No. 2011-128033.
[Patent Document 2]Japanese Patent Publication No. 6156893.

However, even with the nozzles recited in the above-described related art documents, the collection ratio of the analysis solution after scanning may be deteriorated, resulting in a tendency toward adversely affected analysis accuracy. This may occur in analysis of: highly hydrophilic substrates such as semiconductor substrates obtained by bulk etching of a silicon wafer referred to as a "P+ silicon wafer" or "P++ silicon wafer", which has a comparatively high boron content; silicon wafers implanted with ions with a high level of energy; silicon wafers done with dry etching to dissolve organic substances on the silicon wafers; SiC; and glass wafers.

The nozzle of double-tube structure recited in Patent Document 1 is specifically illustrated in FIG. 1. The nozzle 1 illustrated in FIG. 1 has a double-tube structure made up of a nozzle body 10 and an outer tube 20. The nozzle body 10 includes a small tube 11, which is connected to a syringe pump (not illustrated). Through the small tube 11, analysis solution D can be discharged and sucked. The outer tube 20 includes an exhausting means 21, which is connected to a pump (not illustrated) to make a reduced pressure atmosphere in the space between the nozzle body 10 and the outer tube 20. The substrate analysis nozzle illustrated in FIG. 1 is moved to scan the surface of a substrate, which is an analysis subject, using the analysis solution D held in the outer tube 20. During the scanning, the space between the nozzle body 10 and the outer tube 20 is kept at a reduced pressure atmosphere. This prevents the analysis solution D from being released from the gap between the outer tube 20 and the analysis subject substrate, W (wafer). After the scanning of the substrate surface, the reduced pressure state of the space between the nozzle body 10 and the outer tube 20 is stopped, and the analysis solution D is collected through the small tube 11 of the nozzle body 10 by suction. The collected analysis solution is analyzed at an analyzer.

With this nozzle of double-tube structure, because of surface tension, the analysis solution turns into a state of droplets, making analysis of a substrate having a hydrophobic substrate surface possible, with the analysis solution used for scanning and collected without any special problems. In analysis of a substrate having a highly hydrophobic substrate surface, however, it is necessary to make narrow the gap that the substrate W has relative to the nozzle body 10 and the outer tube 20 so as to prevent release of the analysis solution. However, when the analysis solution D is collected through the small tube 11 of the nozzle body 10 by suction after scanning, the analysis solution D existing in the space between the nozzle body 10 and the outer tube 20 may remain in the space between the nozzle body 10 and the outer tube 20, instead of moving into the nozzle body 10. One method of reducing the amount of residual analysis solution is to, at the time of collecting the analysis solution, widen the gap between the nozzle body and the substrate so as to enable the analysis solution D existing in the space between the nozzle body 10 and the outer tube 20 to more easily move into the nozzle body 10. In the case of a highly hydrophilic substrate, however, if the reduced pressure state in the space between the nozzle body 10 and the outer tube 20 is stopped at the time of collecting the analysis solution ID, the analysis solution D may leak out of the outer tube 20.

In the substrate analysis nozzle of double-tube structure recited in Patent Document 2, inactive gas is sprayed toward the tip of the nozzle body of the nozzle in a direction approximately parallel to the substrate surface. This reliably prevents a leakage (i.e. release) of the analysis solution from the tip of the nozzle during scanning of a substrate surface, even a highly hydrophilic substrate surface. However, similarly to Patent Document 1, the analysis solution may remain in the space between the nozzle body and the outer tube at the time of collecting the analysis solution, resulting in a tendency toward a lowered collection ratio of the analysis solution.

SUMMARY

Problems to be Solved by the Invention

In light of the circumstances, the present invention provides a substrate analysis nozzle that reliably prevents a leakage (release) of analysis solution from the nozzle even in the case of a highly hydrophilic substrate and that collects the analysis solution with a high collection ratio after scanning.

Means of Solving the Problems

In order to solve the above-described problems, the present invention is directed to a substrate analysis nozzle configured to discharge an analysis solution from a tip of the substrate analysis nozzle onto a substrate, configured to scan a surface of the substrate using the discharged analysis solution, and configured to suck the analysis solution. The substrate analysis nozzle has a triple-tube structure made up of: a pipe through which the analysis solution is discharged and sucked; a first outer tube surrounding the pipe and surrounding the analysis solution used for scanning; and a second outer tube surrounding the first outer tube. The substrate analysis nozzle includes: first exhausting means including an exhaust path defined between the pipe and the first outer tube; and second exhausting means including an exhaust path defined between the first outer tube and the second outer tube. The present invention ensures that even a highly hydrophilic substrate surface can be scanned without release of analysis solution from the nozzle, and that the analysis solution can be collected at a high collection ratio.

In the present invention, examples of a substrate having a highly hydrophobic substrate surface include highly hydrophilic substrates such as semiconductor substrates obtained by bulk etching of a silicon wafer referred to as a "P+ silicon wafer" or "P++ silicon wafer", which has a comparatively high boron content; silicon wafers implanted with ions with a high level of energy; silicon wafers done with dry etching to dissolve organic substances on the silicon wafers; SiC; and glass wafers. An example of a highly hydrophilic substrate is a substrate having a contact angle of 90° or less.

In an analysis using the substrate analysis nozzle according to the present invention, it is preferable to discharge an analysis solution through a pipe onto a substrate, to scan a surface of the substrate using the discharged analysis solution while exhausting gas using second exhausting means, and to suck the analysis solution containing an analysis subject through the pipe while exhausting gas using first exhausting means. The substrate analysis nozzle according to the present invention has a "triple-tube structure"; in order to scan the substrate surface using analysis solution, the analysis solution is discharged through the pipe onto the substrate, and the substrate surface is scanned using the discharged analysis solution while gas is exhausted using the second exhausting means. This reliably prevents release of analysis solution from the nozzle during scanning. In order to collect the scanned analysis solution, the second exhausting means is stopped, and air is exhausted using the first exhausting means. Also, the gap between the tip of the nozzle and the substrate is widened, and the analysis solution containing an analysis subject is collected by having the analysis solution itself sucked through the pipe. This causes the analysis solution located between the second outer tube and the first outer tube to be sucked into the space between the first outer tube and the nozzle body. If the analysis solution in this state is sucked through the pipe, the analysis solution can be collected at an advantageously high collection ratio.

In the substrate analysis nozzle according to the present invention, there is no particular limitation to the sizes of the elements constituting the triple-tube structure. It is preferable to prepare a substrate analysis nozzle of a size that has been adjusted in a desired manner based on the kind and/or size of the analysis subject substrate and based on analysis conditions. One practical application is that the pipe has an inner diameter of ⅛ inches (the pipe thickness is 0.2 mm to 0.5 mm), the first outer tube has an inner diameter of 10 mm (the thickness of the first outer tube is 1 mm to 2 mm), and the second outer tube has an inner diameter of 20 mm (the thickness of the first outer tube is 1 mm to 2 mm).

Effects of the Invention

As has been described hereinbefore, the substrate analysis nozzle according to the present invention reliably prevents a leakage (release) of analysis solution from the nozzle even in the case of a highly hydrophilic substrate and collects the analysis solution with a high collection ratio after scanning.

MODES FOR CARRYING OUT THE INVENTION

Figure 2:
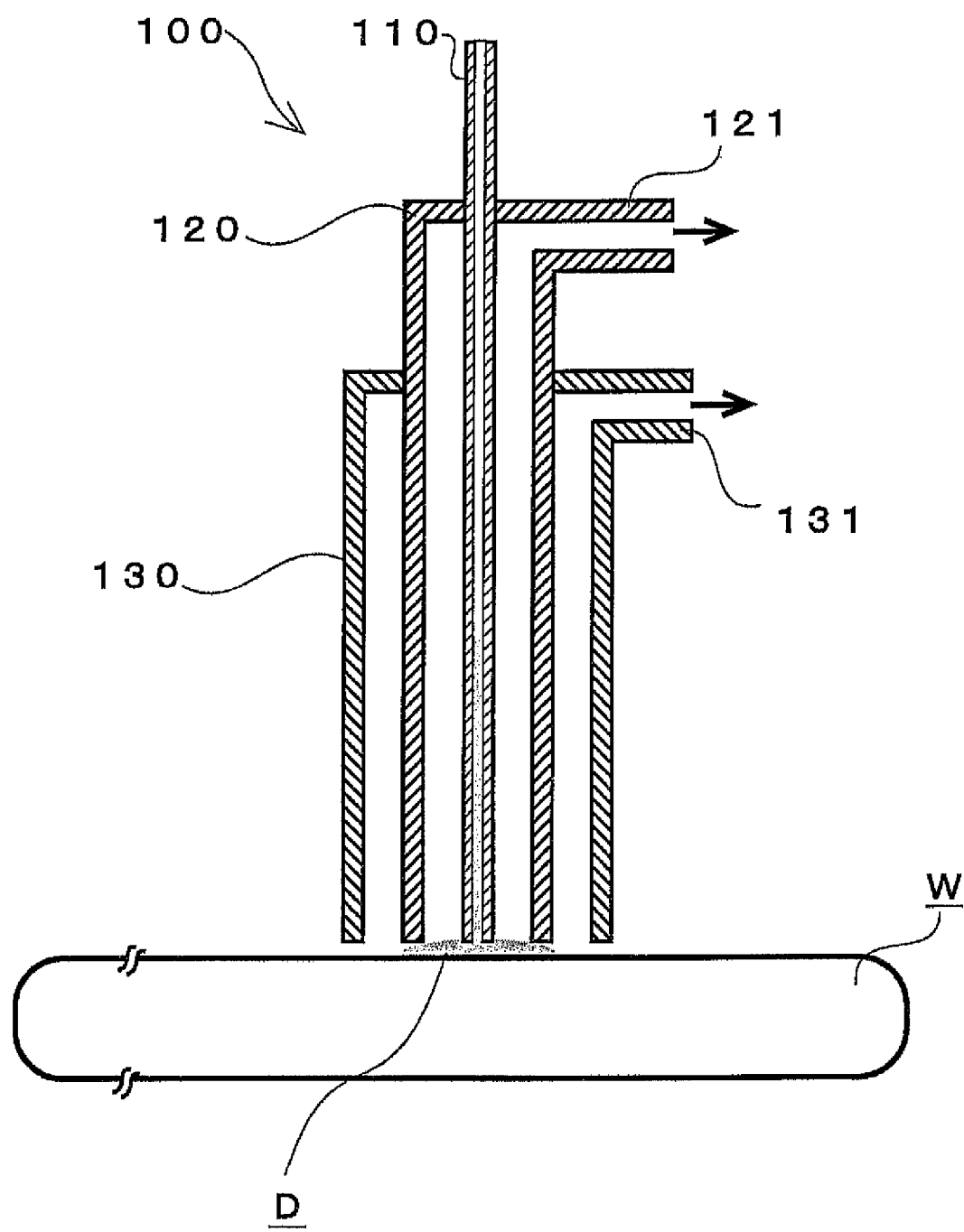
FIG. 2 is a cross-sectional view of a substrate analysis nozzle according to this embodiment.

An embodiment of the present invention will be described below. FIG. 2 illustrates a cross-sectional view of a substrate analysis nozzle according to this embodiment.

The nozzle 100 illustrated in FIG. 2 has a triple-tube structure made up of: a pipe 110; a first outer tube 120, which surrounds the pipe 110; and a second outer tube 130, which surrounds the first outer tube 120. The pipe 110 is connected to a syringe pump (not illustrated) so that analysis solution can be sucked and discharged through the pipe 110.

The first outer tube 120 includes first exhausting means 121, which is connected to an exhaust pump (not illustrated) so that the space (first exhaust path) defined between the pipe 110 and the first outer tube 120 can be turned into a reduced pressure atmosphere. Similarly, second exhausting means 131 is disposed between the first outer tube 120 and the second outer tube 130. The second exhausting means 131 is connected to an exhaust pump (not illustrated) so that the space (second exhaust path) defined between the first outer tube 120 and the second outer tube 130 can be turned into a reduced pressure atmosphere.

Using the nozzle of triple-tube structure according to this embodiment, a substrate analysis is performed according to the following procedure. First, the nozzle 100 is lowered to a position over the substrate, W, while ensuring that the tip of the nozzle 100 is kept out of contact with the substrate surface (the gap between the tip of the nozzle 100 and the substrate W is adjusted at approximately 0.1 mm to 0.2 mm). Then, analysis solution is discharged through the pipe 110. Here, the second exhaust path is kept at a reduced pressure atmosphere. With the second exhaust path in this state, the substrate surface is scanned using the analysis solution. After a predetermined scanning operation has been performed and the nozzle has been stopped, the first exhaust path is turned into a reduced pressure atmosphere while at the same time the reduced pressure state of the second exhaust path is released. Also, the gap between the tip of the nozzle 100 and the substrate W is widened to approximately 1 mm. With the gap in this state, the analysis solution is sucked through the pipe 110, and thus the analysis solution is collected into the syringe pump. The collected analysis solution is analyzed with an analyzer.

Next, description will be made with regard to results of an examination on the collection ratio of analysis solution collected using the substrate analysis nozzle according to this embodiment. The dimensions of the nozzle are as follows. In the nozzle that was used, the outer diameter of the pipe was 1/8 inches, the inner diameter of the first outer tube was 6 mm, the outer diameter of the first outer tube was 12 mm, the inner diameter of the second outer tube was 20 mm, and the outer diameter of the second outer tube was 22 mm. As the analyzed substrate, a 12-inch P++ silicon wafer was used. As the analysis solution, a solution containing 3% HF and 4% $H_2O_2$ was used.

The examination on the collection ratio was performed by measuring the amount of the analysis solution discharged through the pipe and measuring the amount of the analysis solution collected into the nozzle body after the scanning. 1000 μL of analysis solution was introduced into the pipe. With 800 μL of the analysis solution discharged on the analyzed substrate, the analyzed substrate was scanned at a speed of 30 mm/min, and then the analysis solution was collected by suction. The amount of the collected analysis solution was 950 μL. That is, the collection ratio of analysis solution collected using the substrate analysis nozzle according to this embodiment was 95%.

Figure 1:
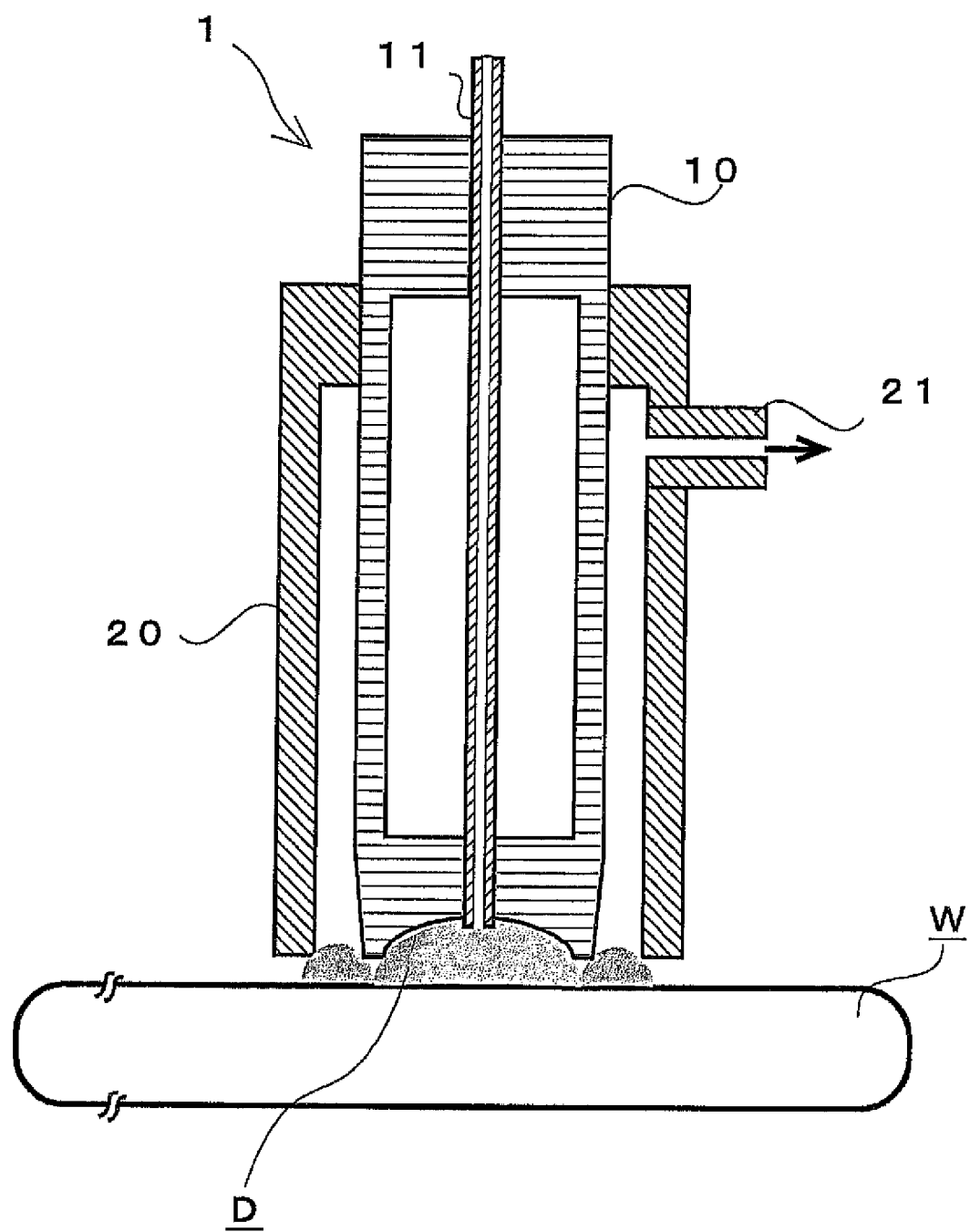
FIG. 1 is a cross-sectional view of a nozzle of double-tube structure.

For comparison purposes, description will be made with regard to a collection ratio obtained using the nozzle of double-tube structure illustrated in FIG. 1. In this nozzle of double-tube structure, the outer diameter of the nozzle body was 12 mm, the inner diameter of the outer tube was 20 mm, and the outer diameter of the first outer tube was 22 mm. The analyzed substrate and the analysis solution were respectively similar to the above-described analyzed substrate and analysis solution. Under the same conditions as those for the above-described embodiment, scanning was performed using the analysis solution, and then the analysis solution was collected by suction. The amount of the collected analysis solution was 700 μL. That is, the collection ratio of analysis solution collected using the nozzle of double-tube structure illustrated in FIG. 1 was 70%.

DESCRIPTION OF REFERENCE NUMERALS 1, 100 Nozzle
10 Nozzle body
11 Small tube
20 Outer tube
110 Pipe
120 First outer tube
130 Second outer tube
W Wafer
D Analysis solution

The invention claimed is:

1. A substrate analysis nozzle configured to discharge an analysis solution from a tip of the substrate analysis nozzle onto a substrate, configured to scan a surface of the substrate using the discharged analysis solution, and configured to suck the analysis solution, wherein the substrate analysis nozzle comprises a triple-tube structure comprising a pipe through which the analysis solution is discharged and sucked; a first outer tube surrounding the pipe and surrounding the analysis solution used for scanning; and a second outer tube surrounding the first outer tube, and wherein the substrate analysis nozzle comprises: first exhausting means comprising an exhaust path defined between the pipe and the first outer tube; and second exhausting means comprising an exhaust path defined between the first outer tube and the second outer tube.

2. A method for analyzing a substrate with a substrate analysis nozzle the method comprising providing a substrate analysis nozzle according to claim 1 and discharging an analysis solution through a pipe onto a substrate; scanning a surface of the substrate using the discharged analysis solution while exhausting gas using the second exhausting means; and stopping the second exhausting means and sucking an analysis solution containing an analysis subject through the pipe while exhausting gas using the first exhausting means.

* * * * *